US008442650B2

(12) United States Patent
Seifert

(10) Patent No.: US 8,442,650 B2
(45) Date of Patent: May 14, 2013

(54) MEDICAL ELECTRICAL LEAD WITH BACKFILLED ELECTRODE SUB-ASSEMBLY

(75) Inventor: Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 398 days.

(21) Appl. No.: 12/627,100

(22) Filed: Nov. 30, 2009

(65) Prior Publication Data

US 2010/0137959 A1     Jun. 3, 2010

Related U.S. Application Data

(60) Provisional application No. 61/118,604, filed on Nov. 29, 2008.

(51) Int. Cl.
*A61N 1/00*     (2006.01)

(52) U.S. Cl.
USPC .......................................................... 607/116

(58) Field of Classification Search .................. 607/119, 607/120, 122
See application file for complete search history.

(56) References Cited

U.S. PATENT DOCUMENTS

| | | | |
|---|---|---|---|
| 4,384,083 A * | 5/1983 | Baker ......................... | 525/420.5 |
| 4,481,953 A | 11/1984 | Gold et al. | |
| 4,603,705 A | 8/1986 | Speicher et al. | |
| 5,016,646 A * | 5/1991 | Gotthardt et al. ............. | 607/122 |
| 5,105,826 A * | 4/1992 | Smits et al. .................... | 607/119 |
| 5,174,288 A | 12/1992 | Bardy et al. | |
| 5,271,417 A | 12/1993 | Swanson et al. | |
| 5,522,872 A | 6/1996 | Hoff | |
| 5,676,694 A | 10/1997 | Boser et al. | |
| 5,728,149 A * | 3/1998 | Laske et al. .................... | 607/122 |
| 5,928,277 A | 7/1999 | Laske et al. | |
| 5,935,159 A | 8/1999 | Cross, Jr. et al. | |
| 5,957,970 A | 9/1999 | Shoberg et al. | |
| 6,016,436 A | 1/2000 | Bischoff et al. | |
| 6,038,463 A | 3/2000 | Laske et al. | |
| 6,038,472 A | 3/2000 | Williams et al. | |
| 6,052,625 A | 4/2000 | Marshall | |
| 6,061,595 A | 5/2000 | Safarevich | |
| 6,181,971 B1 | 1/2001 | Doan | |
| 6,256,542 B1 | 7/2001 | Marshall et al. | |
| 6,259,954 B1 | 7/2001 | Conger et al. | |
| 6,289,251 B1 | 9/2001 | Huepenbecker et al. | |
| 6,615,695 B1 | 9/2003 | Hjelle et al. | |
| 6,697,675 B1 | 2/2004 | Safarevich et al. | |
| 6,704,604 B2 | 3/2004 | Soukup et al. | |
| 6,801,809 B2 | 10/2004 | Laske et al. | |
| 6,813,521 B2 | 11/2004 | Bischoff et al. | |
| 6,920,361 B2 | 7/2005 | Williams | |
| 7,031,777 B2 | 4/2006 | Hine et al. | |
| 7,130,700 B2 | 10/2006 | Gardeski et al. | |
| 7,277,762 B2 | 10/2007 | Belden et al. | |

(Continued)

*Primary Examiner* — Christopher D Koharski
*Assistant Examiner* — Nadia Ahmad
(74) *Attorney, Agent, or Firm* — Reed A. Duthler

(57) ABSTRACT

A medical electrical lead that includes a lead body and at least one tubular electrode sub-assembly positioned over and attached to the external surface of the lead body. The lead body includes at least one elongated conductive element, such as a cable, that is electrically connected to an electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body which may potentially improve flexibility of the medical electrode lead in the area occupied by the tubular electrode sub-assembly.

24 Claims, 8 Drawing Sheets

U.S. PATENT DOCUMENTS

| | | |
|---|---|---|
| 7,474,924 B2 | 1/2009 | Honeck et al. |
| 7,512,447 B2 | 3/2009 | Marshall et al. |
| 2005/0240252 A1 | 10/2005 | Boser et al. |
| 2006/0241734 A1 * | 10/2006 | Marshall et al. ............... 607/122 |
| 2007/0276458 A1 | 11/2007 | Boser |
| 2009/0254162 A1 | 10/2009 | Quinci et al. |

* cited by examiner

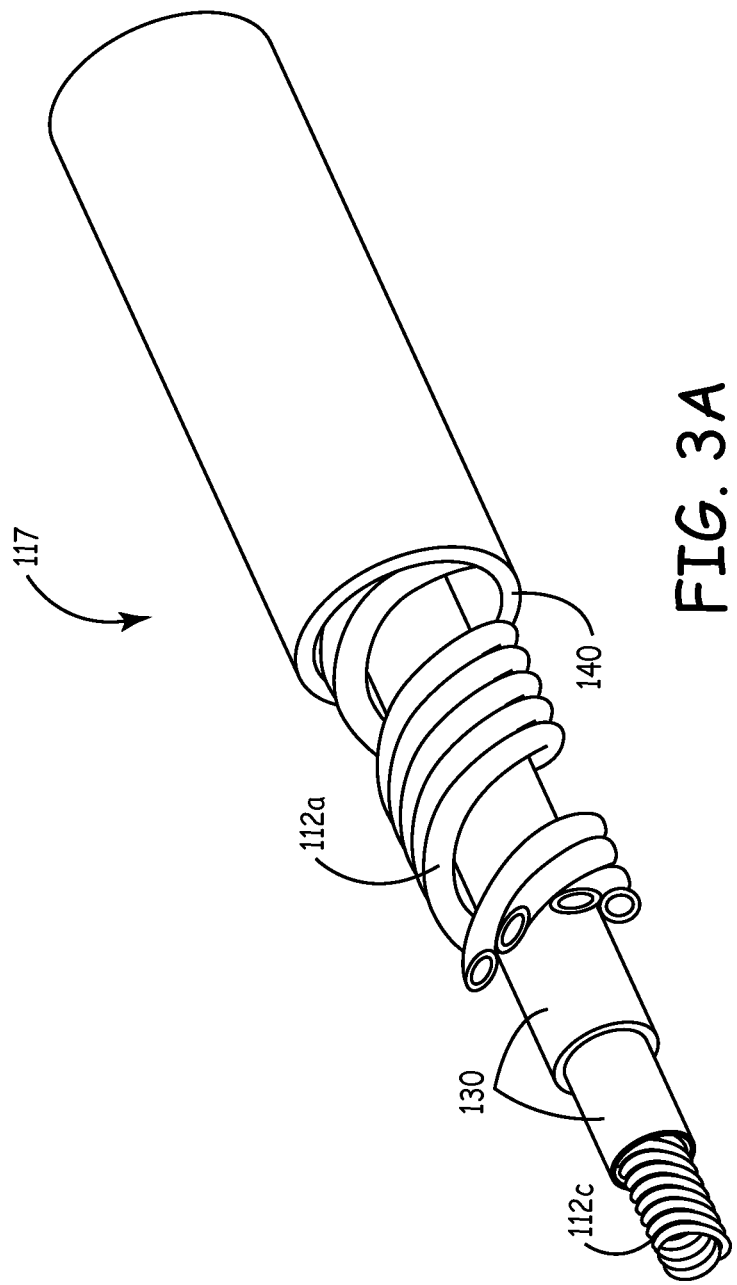

MEDICAL ELECTRICAL LEAD WITH BACKFILLED ELECTRODE SUB-ASSEMBLY

CROSS-REFERENCE TO RELATED APPLICATIONS

This application claims the benefit of U.S. Provisional Application No. 61/118,604, filed on Nov. 29, 2008. The disclosure of the above application is incorporated herein by reference.

TECHNICAL FIELD

This disclosure relates to implantable medical devices and, more particularly, to implantable medical electrical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically include, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead can be inserted through various venous portions so that the tip portion can be positioned at the selected position near or in the muscle group. When therapy is required by a patient, the control module signals the battery to charge the capacitor, which in turn discharges electrical stimuli to tissue of a patient through via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module.

In the context of implantable defibrillators, most systems include large surface area implantable electrodes to be mounted in or adjacent the heart. One common approach of providing a large surface area electrode is to employ an elongated exposed coil of biocompatible metal. In the context of an endocardial lead, this is disclosed in U.S. Pat. No. 4,161, 942 issued to Kinney. In the context of an epicardial lead, this is disclosed in the context of U.S. Pat. No. 4,817,634 issued to Holleman et al.

An elongated coil serving as the electrode is typically mounted around the exterior of an insulative lead body. It is believed desirable in this context to stabilize the electrode coil with respect to the lead body, both to provide mechanical integrity and to prevent fibrous ingrowth around the individual coils of the electrode coil. In the above cited Kinney et al. patent and in U.S. Pat. No. 4,934,049, issued to Keikhafer et al., this is accomplished by sliding the coil over the lead body and backfilling the spaces between the electrode coil with a plastic material. In prior U.S. Pat. No. 5,042,143 issued to Holleman, et al. and U.S. Pat. No. 5,344,708 issued to Bischoff, et al. alternative methods of producing a lead structure similar to that produced in the Keikhafer patent are disclosed. In these patents a plastic tube is stretched. An electrode coil having a inner is then slid over the stretched tube, after which the tube, after which the tube is released, allowing it to return to its previous length. Thereafter, a mandrel is inserted into the tubing, compressing the tubing between the mandrel and the conductor coil. The assembly is thereafter heated, allowing the tubing to flow into spaces between the electrode coil to a desired depth.

U.S. patent application Ser. No. 11/549,284 filed Oct. 13, 2006 by Boser also discloses mechanisms for producing leads employing such electrode

SUMMARY

The present disclosure relates to medical electrical leads that include a lead body and at least one tubular electrode sub-assembly positioned over and attached to the external surface of the lead body. The lead body includes at least one elongated conductive element, such as a cable, that is electrically connected to an electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body which may potentially improve flexibility of the medical electrode lead in the area occupied by the tubular electrode sub-assembly.

The tubular electrode sub-assembly, in some embodiments, may include an organic polymeric tubular liner having an outer surface and a continuous, uninterrupted inner surface that extends from between a proximal end and distal end of the tubular liner, and an electrode located over the outer surface of the polymeric tubular liner, wherein an inner surface of the electrode contacts the outer surface of the tubular liner, interstitial liner material located on the outer surface of the tubular liner in interstices of the electrode, wherein at least a portion of an outer surface of the electrode comprises an exposed outer surface proximate an outer surface of the tubular electrode sub-assembly between the interstitial liner material. The tubular electrode may be attached to underlying structure of the lead body at one or more selected attachment sites over which the tubular electrode sub-assembly is positioned. The one or more selected attachment sites may occupy only a portion of the inner surface of the tubular liner.

The present disclosure also relates to methods of manufacturing medical electrical leads that include manufacturing a tubular electrode sub-assembly by positioning an electrode over an outer liner surface of a tubular liner, wherein the tubular liner is located on a mandrel and includes a continuous, uninterrupted inner liner surface facing the mandrel, delivering a flowable interstitial liner material including a hardenable organic polymer onto the electrode and tubular liner such that the interstitial liner material fills interstices of the electrode and forms an outer liner surface proximate an outer surface of the electrode, hardening the flowable interstitial liner material to form hardened interstitial liner material within the interstices of the electrode, removing the mandrel from the tubular liner after hardening the interstitial liner material, wherein the tubular liner, the interstitial liner material and the electrode form the tubular electrode sub-assembly.

The methods of manufacture may further include positioning the tubular electrode sub-assembly over an external surface of a lead body after manufacturing the tubular electrode sub-assembly such that the inner liner surface faces the external surface of the lead body, wherein the lead body defines a longitudinal axis extending between a proximal end and a distal end of the lead body, and wherein the longitudinal axis extends through the tubular electrode sub-assembly; attaching the tubular electrode sub-assembly to the external surface of the lead body at one or more selected attachment sites, wherein the one or more selected attachment sites occupy only a portion of an inner liner surface; and electrically connecting a conductive element located within an interior of the lead body to the electrode of the tubular electrode sub-assembly.

The principles described herein are applicable to all types of medical electrical leads. For example, the disclosure applies to cardiovascular leads (e.g. high voltage leads, low voltage leads etc.), neurological leads, or other suitable applications. Also, although described with respect to coiled electrodes, other electrode configurations may alternatively be used.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
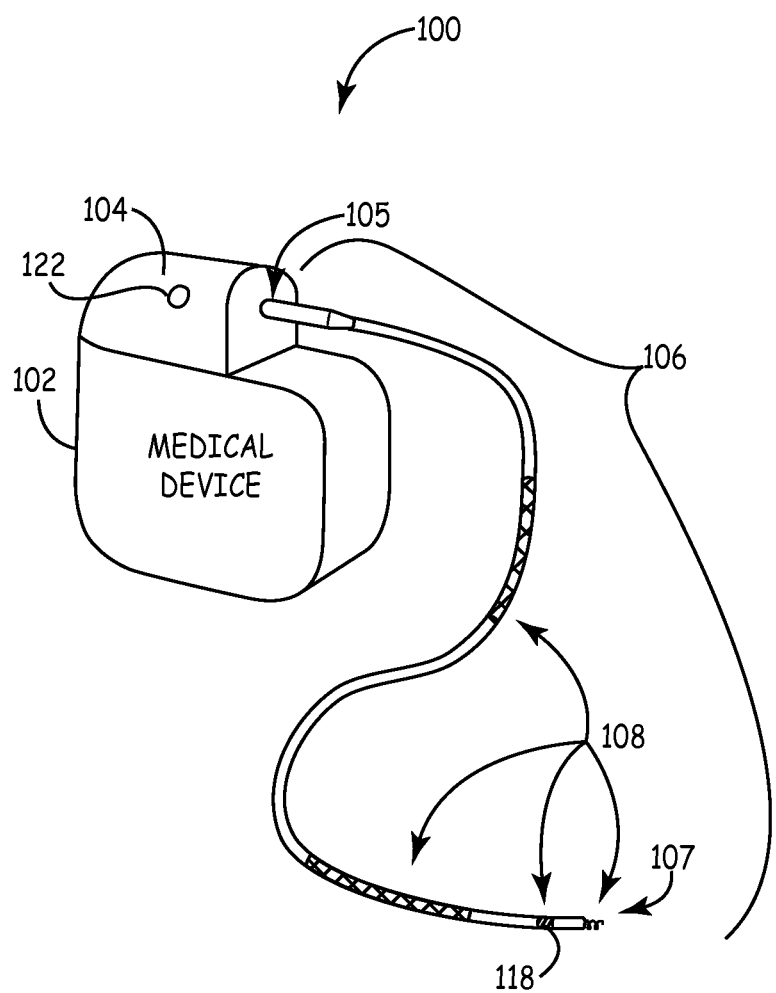
FIG. 1 is a conceptual schematic view of an implantable medical device in which a medical electrical lead extends therefrom.

In the following detailed description, reference is made to the accompanying figures of the drawing which form a part hereof, and in which are shown, by way of illustration, specific embodiments. It is to be understood that other embodiments may be utilized and structural changes may be made without departing from the scope of the present disclosure.

The present disclosure relates to medical electrical leads that include a lead body and at least one tubular electrode sub-assembly positioned over and attached to the external surface of the lead body. The lead body includes at least one elongated conductive element, such as a cable, that is electrically connected to an electrode of the tubular electrode sub-assembly. The tubular electrode sub-assembly includes a tubular liner and an electrode embedded in the outer surface of the liner. In some embodiments, only a portion of the inner surface of the tubular liner is attached to the lead body which may potentially improve flexibility of the medical electrode lead in the area occupied by the tubular electrode sub-assembly.

The tubular electrode sub-assembly, in some embodiments, may include an organic polymeric tubular liner having an outer surface and a continuous, uninterrupted inner surface that extends from between a proximal end and distal end of the tubular liner, and an electrode located over the outer surface of the polymeric tubular liner, wherein an inner surface of the electrode contacts the outer surface of the tubular liner, interstitial liner material located on the outer surface of the tubular liner in interstices of the electrode, wherein at least a portion of an outer surface of the electrode comprises an exposed outer surface proximate an outer surface of the tubular electrode sub-assembly between the interstitial liner material. The tubular electrode may be attached to underlying structure of the lead body at one or more selected attachment sites over which the tubular electrode sub-assembly is positioned. The one or more selected attachment sites may occupy only a portion of the inner surface of the tubular liner.

The present disclosure also relates to methods of manufacturing medical electrical leads that include manufacturing a tubular electrode sub-assembly by positioning an electrode over an outer liner surface of a tubular liner, wherein the tubular liner is located on a mandrel and includes a continuous, uninterrupted inner liner surface facing the mandrel, delivering a flowable interstitial liner material including a hardenable organic polymer onto the electrode and tubular liner such that the interstitial liner material fills interstices of the electrode and forms an outer liner surface proximate an outer surface of the electrode, hardening the flowable interstitial liner material to form hardened interstitial liner material within the interstices of the electrode, removing the mandrel from the tubular liner after hardening the interstitial liner material, wherein the tubular liner, the interstitial liner material and the electrode form the tubular electrode sub-assembly.

The methods of manufacture may further include positioning the tubular electrode sub-assembly over an external surface of a lead body after manufacturing the tubular electrode sub-assembly such that the inner liner surface faces the external surface of the lead body, wherein the lead body defines a longitudinal axis extending between a proximal end and a distal end of the lead body, and wherein the longitudinal axis extends through the tubular electrode sub-assembly; attaching the tubular electrode sub-assembly to the external surface of the lead body at one or more selected attachment sites, wherein the one or more selected attachment sites occupy only a portion of an inner liner surface; and electrically connecting a conductive element located within an interior of the lead body to the electrode of the tubular electrode sub-assembly.

The principles described herein are applicable to all types of medical electrical leads. For example, the disclosure applies to cardiovascular leads (e.g. high voltage leads, low voltage leads etc.), neurological leads, or other suitable applications. Also, although described with respect to coiled electrodes, other electrode configurations may alternatively be used.

FIG. 1 depicts a medical device system 100. A medical device system 100 includes a medical device housing 102 having a connector module 104 (e.g. international standard (IS)-1, defibrillation (DF)-1, IS-4 etc.) that electrically couples various internal electrical components housed in medical device housing 102 to a proximal end 105 of a medical electrical lead 106. A medical device system 100 may comprise any of a wide variety of medical devices that include one or more medical lead(s) 106 and circuitry coupled to the medical electrical lead(s) 106. An exemplary medical device system 100 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIRTUOSO™, RESTORE™, RESTORE ULTRA™, sold by Medtronic, Inc. of Minnesota. Non-implantable medical devices or other types of devices may also utilize batteries such as external drug pumps, hearing aids and patient monitoring devices or other suitable devices. Medical device system 100 may deliver, for example, pacing, cardioversion or defibrillation pulses to a patient via electrodes 108 disposed on distal end 107 of one or more lead(s) 106. Specifically, lead 106 may position one or more electrodes 108 with respect to various cardiac locations so that medical device system 100 can deliver electrical stimuli to the appropriate locations.

Figure 2:
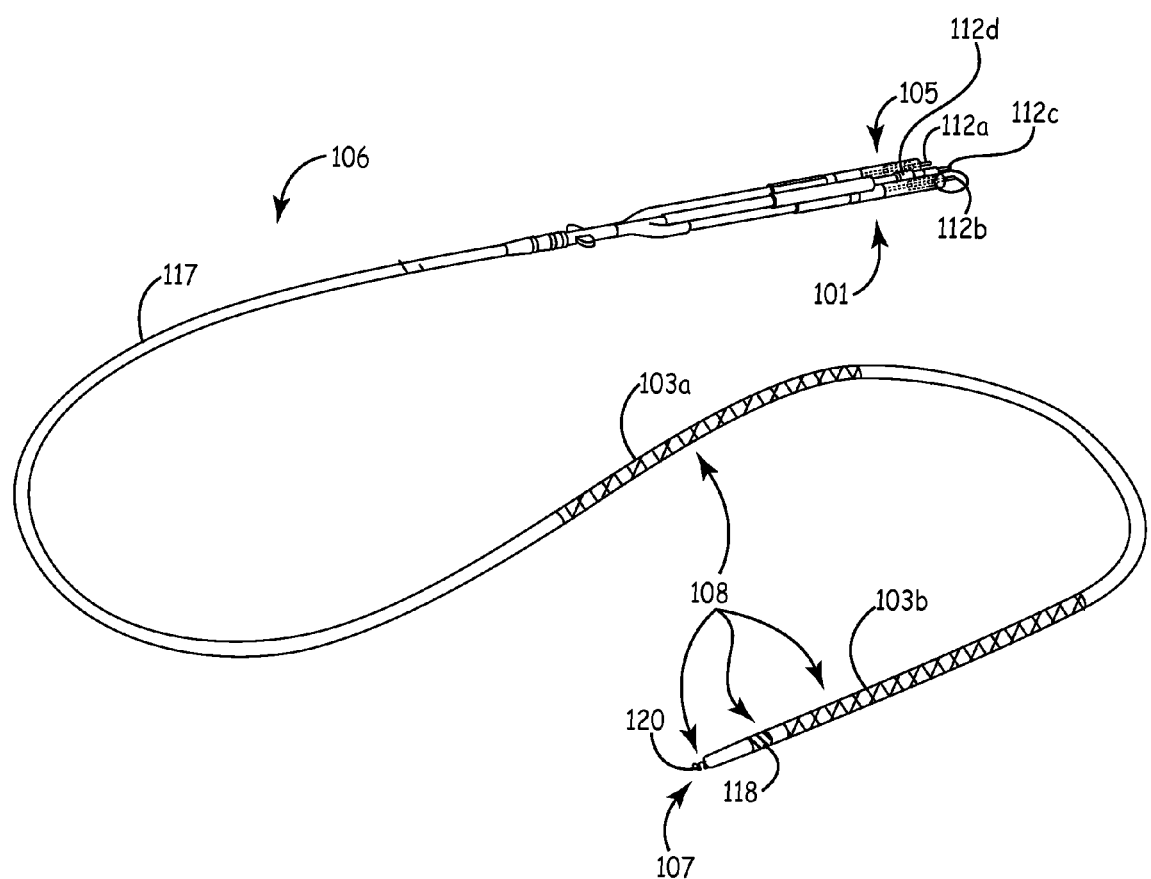
FIG. 2 is a schematic view of a medical electrical lead.

FIG. 2 depicts lead 106. Lead 106 includes a lead body 117 that extends from proximal end 105 to a distal end 107. Lead body 117 can include one or more connectors 101, and one or more jacketed conductive elements 112a-d. A jacket (also referred to as a liner, longitudinal element, coating) extends along and longitudinally around the conductive elements 112a-d and can serve to contain or mechanically constrain one or more conductive elements 112a-d. A jacket can also insulate one or more conductive elements 112a-d. Connector module 104 can contain connectors 122, such as set screws, serve to electrically and mechanically connect conductive elements 112a-d to ports (not shown) of connector module 104. Conductive element 112c (also referred to as a "conductor coil," torque coil", "distal tip conductor") can extend to the distal end 107 and can optionally be coupled to a retractable and/or extendable helical tip. One or more conductive elements 112a,b serve as, or are connected to, defibrillation coils 103a,b that deliver electrical stimuli, when necessary, to tissue of a patient. Lead 106 can also include a conductive element 112d that extends from the proximal end 105 to ring electrode 118 while another conductive element 112c extends from proximal end 105 to tip electrode 120.

Electrically conductive elements that extend along the length of the lead 106 can include coils, wires, coil wound around a filament, cables, conductors or other suitable members. Conductive elements can include platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. The electrically conductive elements are typically covered, or substantially covered, longitudinally with a jacket. In yet another embodiment, each conductive element within the lead body 117 is surrounded by a tubular element within the jacket, which can possess a circular or a non-circular cross-section. Any or all of the components within the lead body 117 can exhibit a non-circular cross-section.

Typically, the outer surface of electrodes 108 such as the ring electrode 118, the tip electrode 120, and the defibrillation electrodes 103a,b are exposed or not covered by a jacket or liner so that electrodes 108 can sense and/or deliver electrical stimuli to tissue of a patient. A sharpened distal tip (not shown) of tip electrode 120 may facilitate fixation of the distal end of helically shaped tip electrode 120 into tissue of a patient.

Figure 3B:
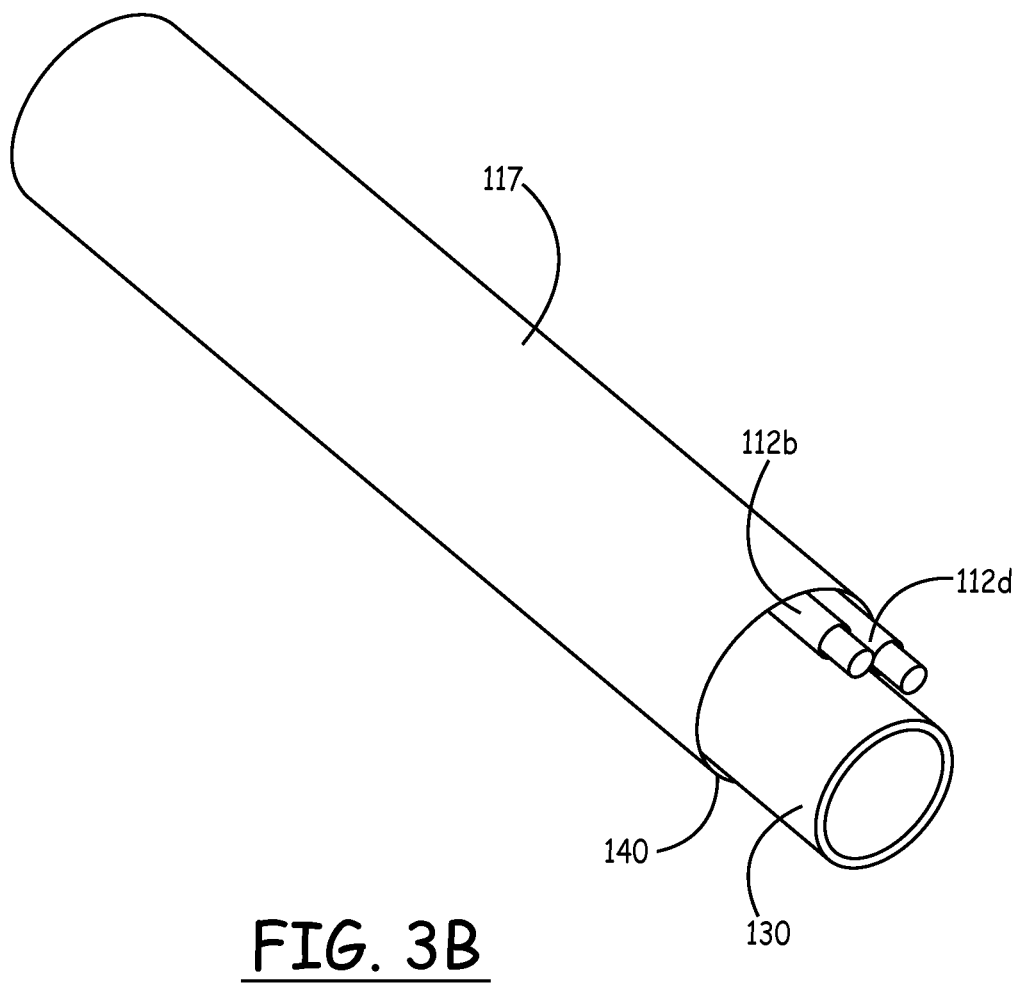
FIG. 3 is a schematic view of a distal end of the medical electrical lead.

FIGS. 3A and 3B depict to examples of lead bodies that may be used in connection with the medical electrical leads of the present disclosure. Referring to FIG. 3A, one example of a lead body 117 is depicted that includes one or more conductive elements 112a and 112c that are provided in a wrapped configuration. The depicted lead body 117 also includes comprises one or more internal jackets 130 with an outer jacket 140 that surrounds the one or more internal jackets 130. FIG. 3B depicts another lead body that includes one or more conductive elements 112b and 112d that extend linearly along the length of the lead body 117. The conductive elements 112b and 112d may be located between an inner structure 130 and an outer jacket 140. In some embodiments, both wrapped and linear conductive elements may be provided in the same lead body. In another embodiment (not pictured) of a lead body that may be used is a multi-lumen tubular structure (symmetric or asymmetric).

Among the electrodes 108, some of the electrodes, such as defibrillation electrodes 103a and 103b, may be provided in the form of coiled electrodes that form a helix, while other electrodes may be provided in different forms. Further, some of the electrodes 108 may be provided in the form of tubular electrode sub-assemblies that can be pre-fabricated and positioned over an existing lead body, where they are attached and where electrical connections with conductive elements within the lead body 117 can be made.

Figure 4:
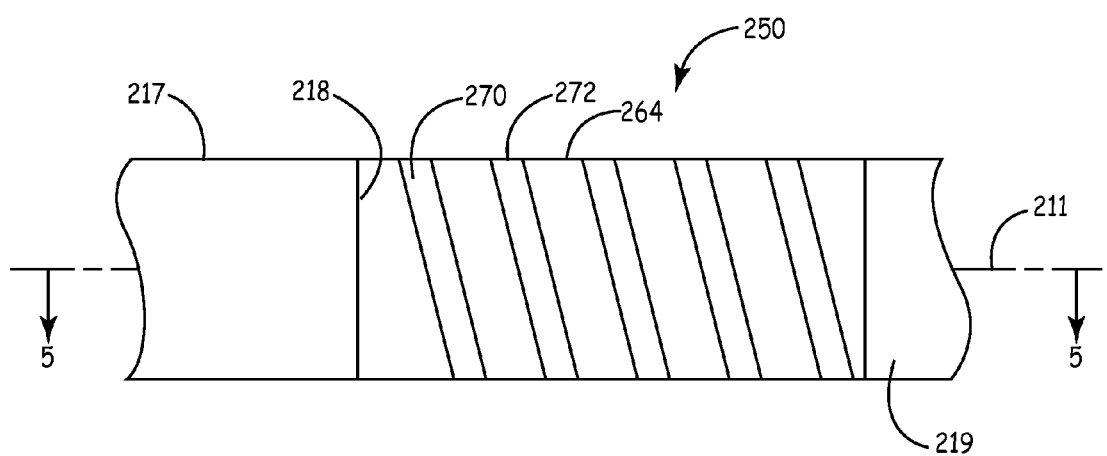
FIG. 4 is a schematic view of a portion of the medical electrical lead that includes a tubular electrode assembly attached thereto.
Figure 5:
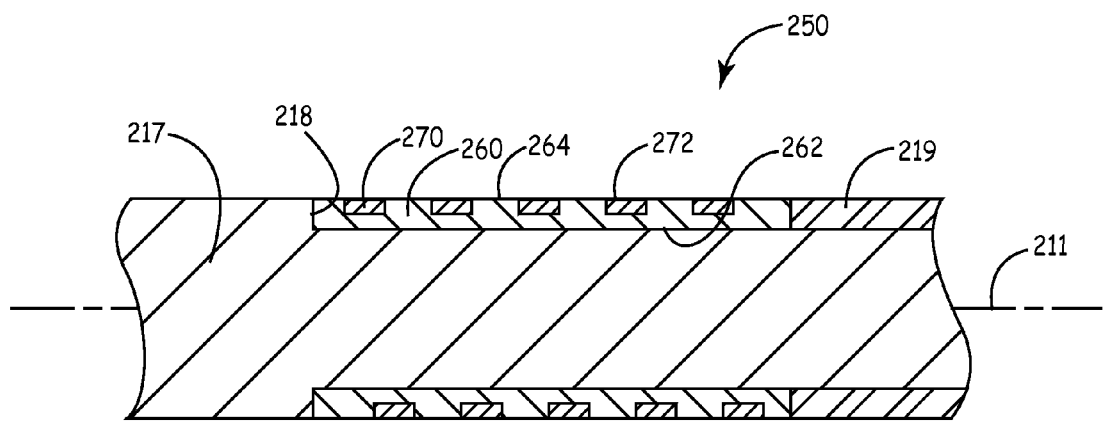
FIG. 5 is a schematic sectional view of the portion of the medical electrical lead of FIG. 4, taken along line 5-5 in FIG. 4.

An example of one such tubular electrode sub-assembly 250 is depicted in FIGS. 4 and 5, where the tubular electrode sub-assembly 250 is positioned over a portion of a lead body 217. The tubular electrode sub-assembly 250 includes a tubular liner 260 and electrode 270 embedded in the outer surface 264 of the tubular liner 260. The electrode 270 is preferably embedded in the outer surface 264 of the tubular liner 260 to a depth that is sufficient to mechanically couple the electrode 270 to the tubular liner 260. At least a portion of the outer surface 272 of the electrode 270 is exposed proximate the outer surface 264 of the tubular liner 260 such that the electrode 270 can be placed in electrical communication with tissue and/or fluids surrounding the tubular electrode sub-assembly 250.

Another optional feature depicted in FIGS. 4 and 5 is that the lead body may be constructed with a variable diameter such that the area in which the tubular electrode sub-assembly 250 is positioned has a reduced size as compared to other portions of the lead body 217. For example, the lead body 217 may include a shoulder as seen in FIG. 5 where the size of the lead body 217 decreases. The diameter of the lead body 217 may be increased on the opposite end of the tubular electrode sub-assembly 250 by optionally including a sleeve 219 or other structure to increase the size of the lead. Such a construction can be used to provide an isodiametric lead, although other constructions could also be used to compensate for the thickness of the tubular electrode sub-assembly 250.

The electrode 270 may, in some embodiments, be formed in the shape of a coil with one or more wraps or coils and using a wire element having a rectangular cross-section as depicted in FIG. 5, although coiled electrodes in other embodiments may be formed using wire elements having any selected shape (e.g., round, oval, elliptical, etc.). The tubular liner 260 may be located between the electrode 270 and the underlying structure of the lead body 217 over a majority of the inner surface 262 of the tubular liner 260. Exceptions to this may occur where, for example, the electrode is connected to a conductive element extending through the lead body 217. That electrical connection may be made by a variety of techniques, with at least some potentially suitable connection techniques being described in US Patent Application Publication Nos. US 2005/0240252 (Boser et al.); US 2005/0113898 (Honeck et al.); etc. The tubular liner 260 may alternatively be characterized as preventing contact between the inner surface of the electrode and the underlying structure of the lead body 217 (except where electrical connections may need to be made as described above).

In yet another manner of characterizing the relationship between the tubular liner 260 and the electrode 270 in some embodiments, the tubular liner 260 can be described as optionally having a liner thickness measured radially from the longitudinal axis 211 between the inner surface 262 and the outer surface 264 of the tubular liner 260. The electrode 270 can be described as having an electrode thickness that is measured radially from the longitudinal axis 211. Further, the liner thickness may be greater than the electrode thickness in some embodiments (as depicted, e.g., in FIG. 5). The tubular liner 260 includes an inner surface 264 that faces the underlying structure of the lead body 217. The tubular electrode sub-assembly 250 is preferably attached to underlying structure of the lead body 217 at one or more selected attachment sites. As discussed herein, the one or more selected attachment sites preferably occupy only a portion of the inner surface 262—in some embodiments, the selected attachment sites may be described as occupying no more than about 50% of the inner surface 262 of the tubular liner 260. By limiting the surface area of attachment between the tubular electrode sub-assembly 250 and the underlying structure of the lead body 217, flexibility of the lead may be improved as compared to a lead in which the entire tubular electrode sub-assembly 250 was attached to the underlying structure of the lead body 217.

Figure 6A:
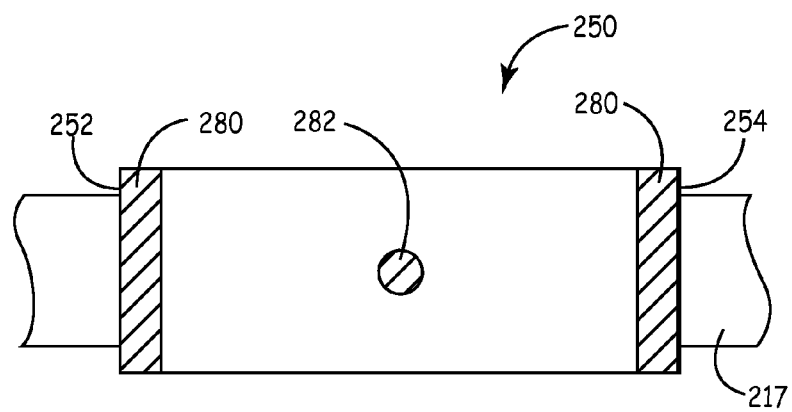
FIG. 6A is a schematic view of a portion of a medical electrical lead including markings to show one arrangement of selected attachment sites where the tubular electrode sub-assembly is attached to the lead body.
Figure 6B:
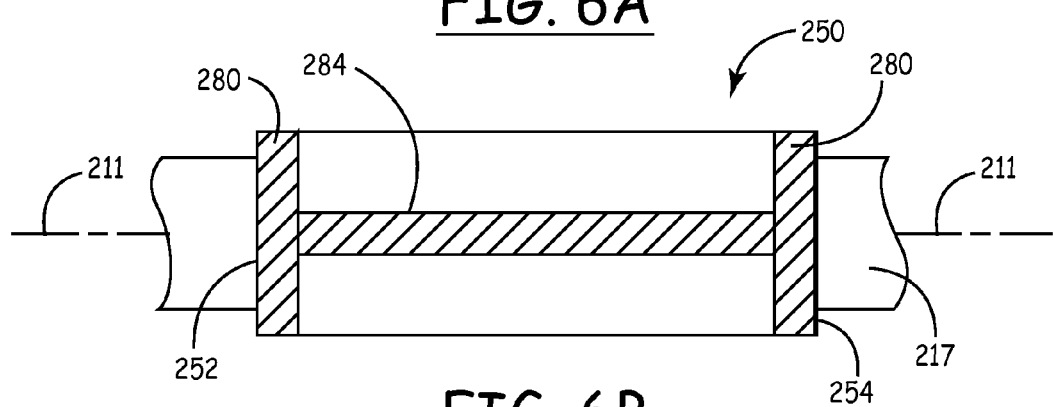
FIG. 6B is a schematic view of a portion of another medical electrical lead including markings to show an alternative arrangement of selected attachment sites where the tubular electrode sub-assembly is attached to the lead body.
Figure 6C:
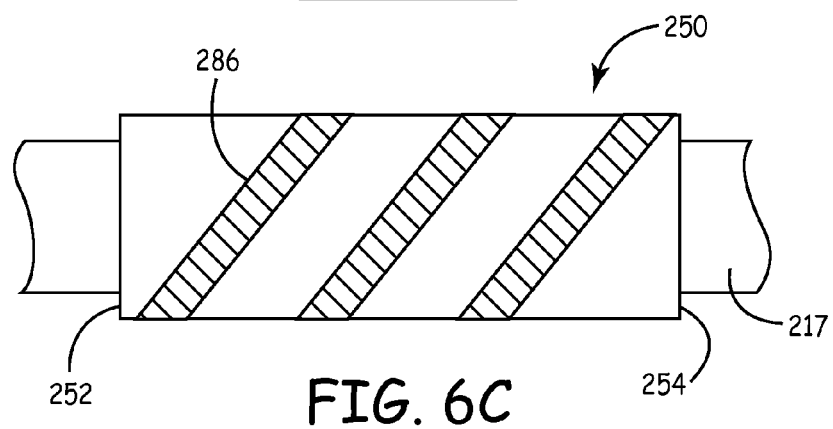
FIG. 6C is a schematic view of a portion of another medical electrical lead including markings to show an alternative arrangement of selected attachment sites where the tubular electrode sub-assembly is attached to the lead body.

FIGS. 6A-6C depict only some of the variations in selection and arrangement of selected attachment sites that may be used to attach the tubular electrode sub-assembly 250 to the underlying lead body 217. The coiled electrode and other features are not depicted in FIGS. 6A-6C for clarity.

In FIG. 6A, the tubular electrode sub-assembly 250 may be attached at its proximal end 252 and its distal end 254 by selected attachment sites 280 that may be in the form of rings around the tubular electrode sub-assembly 250. Although the selected attachment sites 280 at the proximal and distal ends are depicted as continuous rings, they may be provided in any other form, e.g., a group of discrete attachment sites that are arranged around the periphery of the tubular electrode sub-assembly 250 such that a ring structure is formed, etc. The set of selected attachment sites depicted in FIG. 6A may also optionally include one or more intermediate selected attachment sites 282 positioned between the proximal end 252 and the distal end 254 of the tubular electrode sub-assembly 250. Such an intermediate selected attachment site 282 may be provided in combination with attachment sites 280 at the ends of the tubular electrode sub-assembly 250 or one or more intermediate selected attachment sites 282 may be provided in the absence of attachment sites at the ends of the tubular electrode sub-assembly 250.

One potential alternative arrangement of selected attachment sites is depicted in FIG. 6B in which a selected attachment site 284 in the form of a line is depicted in combination with selected attachment sites 280 at the ends of the tubular electrode sub-assembly 250. Although depicted as a straight line that extends from the proximal end 252 to the distal end 254 of the tubular electrode sub-assembly 250 and that is aligned with the longitudinal axis 211, the line 284 may be shorter and/or the line 284 may not be aligned with the longitudinal axis 211. Further, the attachment site 284 may be provided in combination with attachment sites 280 at the ends of the tubular electrode sub-assembly 250 (as depicted) or one or more such lines may be provided in the absence of attachment sites at the ends of the tubular electrode sub-assembly 250.

Another potential alternative arrangement of selected attachment sites is depicted in FIG. 6C in which a selected attachment site 286 is provided in the form of a helix that extends around the tubular electrode sub-assembly 250 and proceeds along its length between the proximal end 252 and the distal end 254. Although the selected attachment site 286 is depicted as a continuous structure, it may be provided in any other form, e.g., a group of discrete attachment sites that are arranged around and along the tubular electrode sub-assembly 250 such that a helical structure is formed, etc. Additional selected attachment sites may also be provided in combination with a helical selected attachment site 286.

In still another alternative, limiting the area occupied by the attachment sites between the tubular electrode sub-assembly 250 and the underlying structure of the lead body may not be used if, for example, the tubular electrode sub-assembly 250 is attached to the underlying structure of the lead body by an attachment agent that has a lower modulus than the material used to construct the liner 260 of the tubular electrode sub-assembly 250. For example, using a silicone medical adhesive to attach the inner surface of the liner 260 to the underlying structure of the lead body 217 may provide sufficient compliance to provide enhanced flexibility in the lead such that the attachment agent (e.g., silicone adhesive, etc.) may occupy more than about 50% of the surface are occupied by the tubular electrode sub-assembly 250. In some embodiments, the attachment agent may be provided over substantially all of the interface between the inner surface of the liner 260 and the underlying structure of the lead body 217.

As discussed herein, the coiled electrode 270 is embedded within a tubular liner 260 that includes an inner liner and interstitial liner material located in the interstices between adjacent coils of the coiled electrode. One potential method for manufacturing a tubular electrode sub-assembly having such a construction is depicted and will be described in connection with FIGS. 7A-7C, which are sectional views taken during different stages of the manufacturing process.

The process begins with an electrode 270 that is located over the outer surface of an inner liner 266 that is, in one embodiment, located over a mandrel 290.

The inner liner 266 may be formed directly on the mandrel 290 or it may be preformed and then placed over the mandrel 290. The inner liner is formed from a hardenable organic polymeric material (e.g., thermoplastic or thermoset) that has a relatively low modulus (i.e., low stiffness, low durometer) for good flexibility of the final assembly, and has a relatively low viscosity for good mold-filling properties. The inner liner may, in some embodiments, have a thickness of about 0.001" to about 0.0015" on the mandrel 290, although in other embodiments, the inner liner 266 may be thicker, e.g., in the range of 0.006" or more.

In one embodiment, the inner liner 266 may be formed directly on the mandrel 290 by dip-coating or otherwise applying a thinned silicone solution (where the thinning is performed using a solvent, e.g., heptane, etc.). Other methods of manufacturing may also be used to form the inner liner 266, e.g., spray coating, coextrusion, extrusion, etc. The electrode 270 may be preformed into a coiled helix or other shape such that the mandrel 290 is inserted into the electrode 270. In some embodiments, the electrode may be formed into a desired shape directly on the inner liner 266 on the mandrel by, e.g., winding an element to form a coiled electrode directly on the inner liner 266 on the mandrel 290 or using any other forming process needed to create an electrode with the desired shape.

Figure 7A:
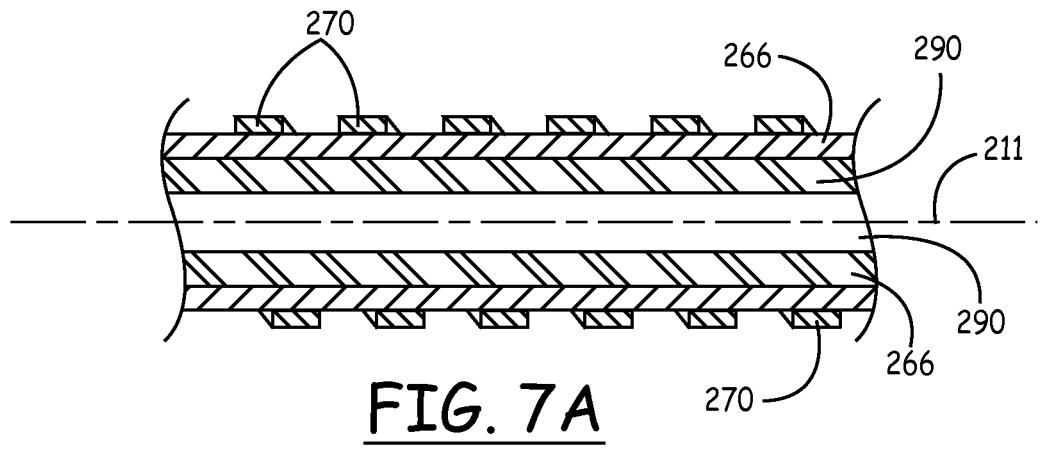
FIG. 7A is a schematic sectional view of a process for forming a tubular electrode sub-assembly with a backfilled electrode in which the electrode is mounted on an inner liner that is provided on a mandrel.
Figure 7B:
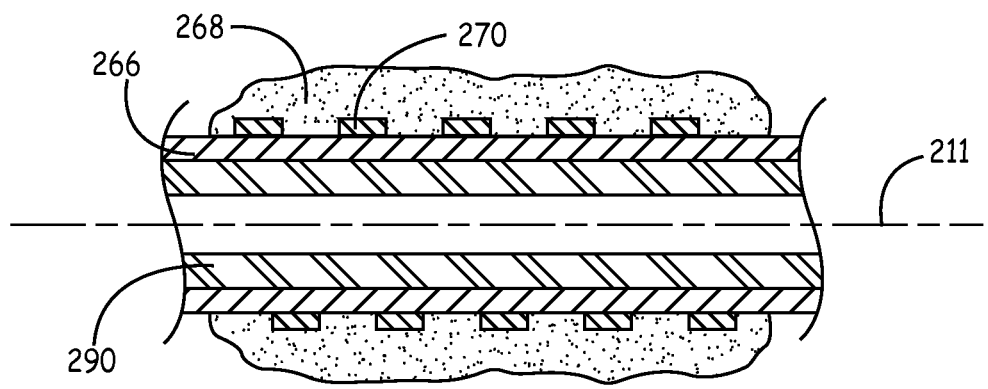
FIG. 7B is a schematic sectional view of FIG. 7A after flowable interstitial liner material has been delivered onto the electrode assembly of FIG. 7A.

With the electrode 270 in position on the inner liner 266, flowable interstitial liner material 268 is delivered onto the assembly of FIG. 7A, resulting in the assembly depicted in FIG. 7B. Delivery of the flowable interstitial liner material 268 may be accomplished by any suitable technique or combination of techniques, e.g., the assembly of FIG. 7A may be rolled in the material 268, the material 268 may be extruded, sprayed, spread, brushed, dispensed, molded or otherwise delivered onto the electrode 270 and inner liner 266.

With the material 268 located on the electrode 270 and the inner liner 266, the excess material 268 may be removed such that the material 268 remains only in the interstices of the coiled electrode 270. In one embodiment, the removal may be performed before the flowable interstitial material 268 is hardened (e.g., cured, cooled, or dried). The removal may also involve clearing the material 268 from the outer surface 272 of the coiled electrode 270 such that the outer surface 272 is exposed. Alternatively, the the removal may be accomplished after hardening by any suitable technique or combination of techniques, e.g., wiping, scraping, buffing, abrading, laser ablation, etc.

After the removal process, a portion of the flowable interstitial material 268 remains in the interstices of the electrode 270. The remaining material 268 is then hardened. After hardening, the electrode 270 is located on the inner liner 266 with the interstitial spaces of the electrode 270 being occupied by the interstitial liner material 268. As a result, the liner 260 (see, e.g., FIGS. 4 and 5) is constructed as a composite of both the inner liner 266 and the interstitial liner material 268. The composition of the inner liner 266 and the interstitial liner material 268 may be the same or different, although in some embodiments the materials used for both components may adhere or bond to each other such that separation of the interstitial liner material 268 from the underlying outer surface of the inner liner 266 is difficult, if not impossible.

After the interstitial liner material 268 has been removed and hardened, the mandrel 290 may be removed from within the inner liner 266. The mandrel removal may be accomplished by a variety of techniques that may include, e.g., deformation, dissolution, etc. If the mandrel 290 is, e.g., a structure that necks down when elongated along the axis 211, then the removal process may involve stretching the mandrel 290 along the axis 211 such that it necks down. The mandrel 290 may be made of material that releases cleanly from the inner liner 266. For example, the mandrel 290 may be manufactured of a metal, such as annealed copper or silver-plated copper wire, coated with an organic polymer to facilitate release from the liner. Such coating materials include PTFE-based coatings, polyimide, or other polymeric coatings such as "PD Slick" coating materials. In some embodiments, the mandrel 290 may be provided in the form of a hollow polymeric tube made of, e.g., ethylene tetrafluoroethylene (ETFE), polytetrafluoroethylene (PTFE), or fluorinated ethylene propylene (FEP). The mandrel may be provided in the form of hollow tube, solid tube, etc.

Figure 7C:
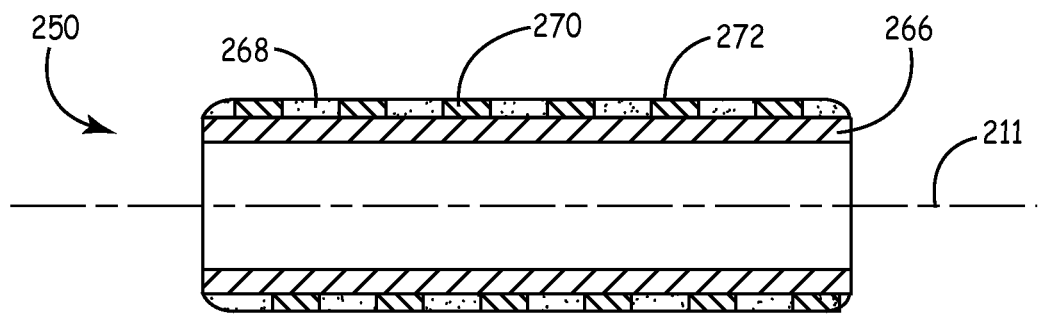
FIG. 7C is a schematic sectional view of a tubular electrode sub-assembly 250 manufactured after processing the assembly of FIG. 7C.
Figure 8:
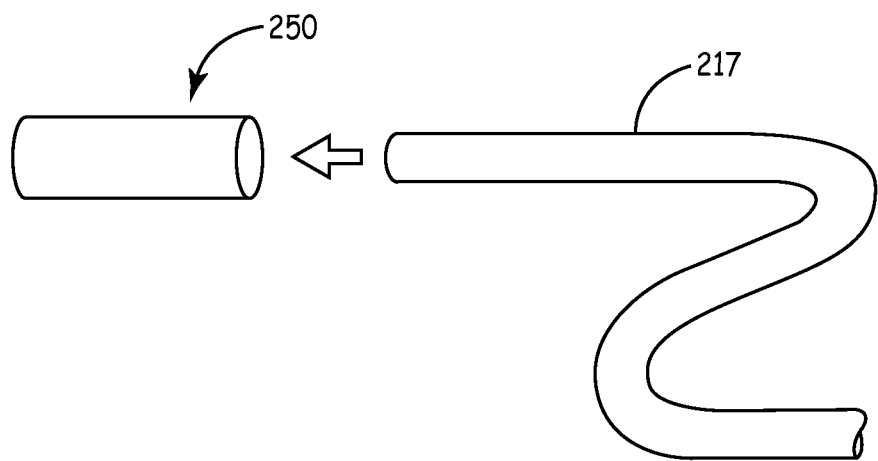
FIG. 8 is a schematic view of a process for placing a tubular electrode sub-assembly onto a lead body.

After the mandrel 290 is removed from the electrode 270 and the composite liner, the finished tubular electrode sub-assembly 250 is obtained as depicted in FIG. 7C. Any further processing may be performed to place the tubular electrode sub-assembly 250 in condition to be placed over a lead body as depicted in FIG. 8 and attached thereto in one or more selected attachment sites as described herein. Such processing to prepare the tubular electrode sub-assembly 250 for attachment to a lead body 217 may include, trimming the tubular electrode sub-assembly 250 to a selected length, preparing the ends or other portions of the coiled electrode for attachment to a conductive element within the lead body 217, etc.

Attachment of the tubular electrode sub-assembly 250 to a lead body 217 may be accomplished using any suitable technique or combination of techniques. In some embodiments, the tubular electrode sub-assembly 250 may be attached to the lead body 217 by welding or otherwise fusing the material of the liner 260 to the lead body 217. Such welding may be performed using any suitable technique or combination of techniques, e.g., ultrasonically, thermally, chemically (using, e.g., solvents), etc.

Another potential technique for providing the selected attachment sites between the tubular electrode sub-assembly 250 and the lead body 217 may be through the use of adhesive. Exemplary adhesive may include silicones, urethanes, fluoropolymers, etc. The adhesives could include those activated via thermal, UV light, chemical, moisture, and solvent-based methods.

The inner liner 266 provided on the mandrel 290 may be formed of any suitable hardenable organic polymeric material that has a relatively low modulus (i.e., low stiffness, low durometer) for good flexibility of the final assembly, and has a relatively low viscosity (e.g., "pre-cure" viscosity) for good mold-filling properties. The inner liner may be formed of a thermoset or a thermoplastic material that can be extruded or processed into a tube. Examples include silicones, polyimides, epoxies, polyurethanes, polyurethanes with surface-modifying end groups (SME), polyurethane silicone block copolymers (e.g., a thermoplastic silicone polyether urethane available under the designation PurSil), fluoropolymers and fluoroelastomers (e.g., ethylene tetrafluoroethylene (ETFE), polytetrafluoroethylene (PTFE), polyvinylidine difluoride (PVDF), Dyneon's THV (a polymer of tetrafluoroethylene, hexafluoropropylene and vinylidene fluoride), Daikin's T-530 fluoroelastomer, and other fluoropolymers and fluoroelastomers), polyethylenes, and polyesters.

In some embodiments, a thermoset material, such as low consistency silicones (e.g., those available under the trade designations MED-4719 or MED-4755 from NuSil), liquid silicone rubber (LSR) (such as Dow Corning's Q7-4850 or NuSil's MED-4850), and "SI polyimide" as described in U.S. Pat. No. 5,639,850 and U.S. Pat. Pub. No. 2005/0004643 (para 17), can be used for the inner liner. In some embodiments, a thermoplastic material, such as polyurethane silicone block copolymers (such as PurSil silicone polyether urethane, a polyurethane, a polyurethane with surface-modifying end groups, and ETFE), can be used for the inner liner.

The flowable interstitial liner materials used in the tubular electrode sub-assemblies of the present disclosure may be selected from a wide variety of materials. Such materials may be the same or different than the materials used for the inner liner described above. Using one material for both the inner liner and the interstitial liner may be easier and more desirable in terms of number of manufacturing steps required; however, it may be desirable to have one material for increased flexibility, mechanical strength and fatigue resistance, dielectric strength, to facilitate bonding to lead body, etc., and a different material more suitable for direct tissue contact.

Fabrication of an electrode sub-assembly using a thermosetting (i.e., thermoset) material typically involves the application of thermal energy to cure the material after the application of pressure or reduced pressure to cause the material to flow and fill the interstitial spaces. Fabrication of an electrode assembly and using a thermoplastic material typically involves the simultaneous application of heat and pressure to cause the material to flow and fill the interstitial spaces. The conditions needed (e.g., time, temperature, pressure), depend on the selection of the material and can be readily determined. Note also that some materials can be hardened or cured (e.g., crosslinked) without application of heat. These include, e.g., silicone medical adhesive or other room temperature vulcanized (RTV) silicone systems, and e-beam irradiated ETFE or other fluoropolymers and fluoroelastomers.

The electrodes used in the tubular electrode sub-assemblies may be selected from a wide variety of electrically conductive biocompatible materials (including, but not limited to, titanium, stainless steel, tantalum, platinum, etc. and combinations thereof (e.g., platinum-iridium clad tantalum, etc.)) that can be formed to take on any selected shape, e.g., a coiled helical shape. Examples of some potentially suitable materials may include, e.g., round wire coils (with a diameter of, e.g., 0.005") and/or flat wire coils (with dimensions of, e.g., 0.003" by 0.007").

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a leg clamp may refer to one or more leg clamps unless otherwise indicated.

The term "and/or" means one or all of the listed elements or a combination of any two or more of the listed elements.

The complete disclosure of the patents, patent documents, and publications identified herein are incorporated by reference in their entirety as if each were individually incorporated.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A medical electrical lead comprising:
a lead body that comprises a length between proximal end and a distal end, wherein the lead body defines a longitudinal axis extending between the proximal end and the distal end;
a conductive element located within an interior of the lead body and extending along the longitudinal axis for at least a portion of the length of the lead body;
a tubular electrode sub-assembly positioned over a portion of the lead body such that the longitudinal axis extends through the tubular electrode sub-assembly, wherein the tubular electrode sub-assembly comprises:
an organic polymeric tubular liner comprising an outer surface and a continuous, uninterrupted inner surface that extends from between a proximal end and distal end of the tubular liner, and
an electrode located over the outer surface of the polymeric tubular liner, wherein an inner surface of the electrode contacts the outer surface of the tubular liner;
interstitial liner material located on the outer surface of the tubular liner in interstices of the electrode;
wherein at least a portion of an outer surface of the electrode comprises an exposed outer surface proximate an outer surface of the tubular electrode sub-assembly between the interstitial liner material;
one or more selected attachment sites at which the tubular electrode sub-assembly is positioned over and attached to underlying structure of the lead body, wherein the one or more selected attachment sites occupy only a portion of the inner surface of the tubular liner; and
an electrical connection within the medical electrode lead between the coiled electrode and the conductive element.

2. The medical electrical lead of claim 1, wherein the tubular liner is located between the electrode and the underlying structure of the lead body.

3. The medical electrical lead of claim 1, wherein the tubular liner prevents contact between the inner surface of the electrode and the underlying structure of the lead body.

4. A medical electrical lead comprising:
a lead body that comprises a length between proximal end and a distal end, wherein the lead body defines a longitudinal axis extending between the proximal end and the distal end;
a conductive element located within an interior of the lead body and extending along the longitudinal axis for at least a portion of the length of the lead body;
a tubular electrode sub-assembly positioned over a portion of the lead body such that the longitudinal axis extends through the tubular electrode sub-assembly, wherein the tubular electrode sub-assembly comprises:
an organic polymeric tubular liner comprising an outer surface and a continuous, uninterrupted inner surface that extends from between a proximal end and distal end of the tubular liner, and
an electrode located over the outer surface of the polymeric tubular liner, wherein an inner surface of the electrode contacts the outer surface of the tubular liner;
interstitial liner material located on the outer surface of the tubular liner in interstices of the electrode;
wherein at least a portion of an outer surface of the electrode comprises an exposed outer surface proximate an outer surface of the tubular electrode sub-assembly between the interstitial liner material;
one or more selected attachment sites at which the tubular electrode sub-assembly is positioned over and attached to underlying structure of the lead body, wherein the one or more selected attachment sites occupy only a portion of the inner surface of the tubular liner; and an electrical connection within the medical electrode lead between the coiled electrode and the conductive element; and wherein the one or more selected attachment sites comprise the proximal end and the distal end of the tubular liner.

5. The medical electrical lead of claim 1, wherein the one or more selected attachment sites comprise the proximal end of the tubular liner, the distal end of the tubular liner, and an intermediate location between the proximal end and the distal end of the tubular liner.

6. A medical electrical lead comprising:
a lead body that comprises a length between proximal end and a distal end, wherein the lead body defines a longitudinal axis extending between the proximal end and the distal end;
a conductive element located within an interior of the lead body and extending along the longitudinal axis for at least a portion of the length of the lead body;
a tubular electrode sub-assembly positioned over a portion of the lead body such that the longitudinal axis extends through the tubular electrode sub-assembly, wherein the tubular electrode sub-assembly comprises:
an organic polymeric tubular liner comprising an outer surface and a continuous, uninterrupted inner surface that extends from between a proximal end and distal end of the tubular liner, and
an electrode located over the outer surface of the polymeric tubular liner, wherein an inner surface of the electrode contacts the outer surface of the tubular liner;
interstitial liner material located on the outer surface of the tubular liner in interstices of the electrode;
wherein at least a portion of an outer surface of the electrode comprises an exposed outer surface proximate an outer surface of the tubular electrode sub-assembly between the interstitial liner material;
one or more selected attachment sites at which the tubular electrode sub-assembly is positioned over and attached to underlying structure of the lead body, wherein the one or more selected attachment sites occupy only a portion of the inner surface of the tubular liner; and
an electrical connection within the medical electrode lead between the coiled electrode and the conductive element; and
wherein the one or more selected attachment sites occupy no more than about 50% of the inner surface of the tubular liner.

7. The medical electrical lead of claim 1, wherein at least one selected attachment site of the one or more selected attachment sites is in the form of a line extending along at least a portion of a length of the tubular liner between the proximal end and the distal end of the tubular liner.

8. The medical electrical lead of claim 7, wherein the line extends from the proximal end of the tubular liner to the distal end of the tubular liner.

9. The medical electrical lead of claim 7, wherein the line is aligned with the longitudinal axis.

10. The medical electrical lead of claim 7, wherein the line comprises a helix formed around the longitudinal axis.

11. The medical electrical lead of claim 1, wherein the polymeric tubular liner comprises a thermoset material.

12. The medical electrical lead of claim 1, wherein the polymeric tubular liner comprises a thermoplastic material.

13. The medical electrical lead of claim 1, wherein the interstitial liner material is the same as the polymeric material of the tubular liner.

14. The medical electrical lead of claim 1, wherein the tubular liner comprises an organic polymeric material selected from the group consisting of polyurethanes, polyurethanes with surface-modifying end groups, polyurethane silicone block copolymers, fluoropolymers, fluoroelastomers, polyethylenes, and polyesters.

15. The medical electrical lead of claim 1, wherein the interstitial liner comprises an organic polymeric material selected from the group consisting of polyurethanes, polyurethanes with surface-modifying end groups, polyurethane silicone block copolymers, fluoropolymers, fluoroelastomers, polyethylenes, and polyesters.

16. The medical electrode lead of claim 1, wherein at least one selected attachment site of the one or more selected attachment sites comprises a welded bond between the tubular liner and the lead body.

17. The medical electrical lead of claim 1, wherein at least one selected attachment site of the one or more selected attachment sites comprises adhesive located between the inner surface of the tubular liner and the external surface of the lead body.

18. The medical electrical lead of claim 1, wherein the electrode comprises a coiled helical electrode.

19. The medical electrical lead of claim 1, wherein the underlying structure of the lead body over which the tubular liner is positioned comprises an outer jacket covering the conductive element located within an interior of the lead body.

20. The medical electrical lead of claim 4, wherein the underlying structure of the lead body over which the tubular liner is positioned comprises an outer jacket covering the conductive element located within an interior of the lead body.

21. The medical electrical lead of claim 6, wherein the underlying structure of the lead body over which the tubular liner is positioned comprises an outer jacket covering the conductor of the lead body.

22. The medical electrical lead of claim 7, wherein the underlying structure of the lead body over which the tubular liner is positioned comprises an outer jacket covering the conductive element located within an interior of the lead body.

23. The medical electrical lead of claim 16, wherein the underlying structure of the lead body over which the tubular liner is positioned comprises an outer jacket covering the conductive element located within an interior of the lead body.

24. The medical electrical lead of claim 17, wherein the underlying structure of the lead body over which the tubular liner is positioned comprises an outer jacket covering the conductive element located within an interior of the lead body.

* * * * *